(12) United States Patent
Yu et al.

(10) Patent No.: US 9,207,175 B2
(45) Date of Patent: Dec. 8, 2015

(54) CONDENSING-TYPE PORTABLE FLUORESCENCE DETECTION SYSTEM

(71) Applicant: KAIST (Korea Advanced Institute of Science and Technology), Daejeon (KR)

(72) Inventors: Kyoungsik Yu, Daejeon (KR); Byounghun Park, Daejeon (KR); Kyungmook Kwon, Daejeon (KR)

(73) Assignee: KAIST (Korea Advanced Institute Of Science And Technology), Daejeon (KR)

( * ) Notice: Subject to any disclaimer, the term of this patent is extended or adjusted under 35 U.S.C. 154(b) by 233 days.

(21) Appl. No.: 13/716,065

(22) Filed: Dec. 14, 2012

(65) Prior Publication Data
US 2014/0014855 A1    Jan. 16, 2014

(30) Foreign Application Priority Data

Jul. 12, 2012 (KR) .................. 10-2012-0075904

(51) Int. Cl.
*G01N 21/64* (2006.01)

(52) U.S. Cl.
CPC .............. *G01N 21/64* (2013.01); *G01N 21/645* (2013.01); *G01N 2201/0221* (2013.01)

(58) Field of Classification Search
CPC ................................ G01N 21/00; G01N 21/64
USPC ........... 250/458.1, 459.1, 461.1, 461.2, 465.1
See application file for complete search history.

(56) References Cited

U.S. PATENT DOCUMENTS

| | | | | |
|---|---|---|---|---|
| 3,677,621 A | * | 7/1972 | Smith | 359/485.07 |
| 4,322,621 A | * | 3/1982 | Aagard | 250/343 |
| 4,954,722 A | * | 9/1990 | Fine et al. | 250/559.06 |
| 4,999,513 A | * | 3/1991 | Ito et al. | 250/575 |
| 5,123,731 A | * | 6/1992 | Yoshinaga et al. | 356/73 |
| 5,231,533 A | * | 7/1993 | Gonokami et al. | 359/328 |
| 5,292,483 A | * | 3/1994 | Kaye | 422/82 |
| 5,366,858 A | * | 11/1994 | Koizumi et al. | 435/5 |
| 5,408,307 A | * | 4/1995 | Yamamoto et al. | 356/73 |
| 5,430,571 A | * | 7/1995 | Witteveen | 359/216.1 |
| 5,506,416 A | * | 4/1996 | Rizvi | 250/339.06 |

(Continued)

FOREIGN PATENT DOCUMENTS

KR    1020120114876    10/2012

OTHER PUBLICATIONS

Kwon, K., et al., Fluorescence detection system with miniaturized integrating sphere, 2011 International Conference on Optical MEMS and Nanophotonics (OMN), 2011, pp. 235-236.

*Primary Examiner* — Marcus Taningco
*Assistant Examiner* — Djura Malevic
(74) *Attorney, Agent, or Firm* — IP & T Group LLP

(57) ABSTRACT

A condensing-type portable fluorescence detection system which detects antigens using fluorescence includes: a light source generating light to excite a fluorescent substance; a first filter selecting a proper wavelength range from the light generated from the light source; a spherical mirror including two hemispherical mirrors having different curvature radiuses and connected to each other, and condensing the light excited and emitted from the light source; a second filter selecting a proper wavelength range of the light condensed by the spherical mirror; and a photodetector detecting fluorescence from the light condensed by the spherical mirror and passing through the second filter.

10 Claims, 9 Drawing Sheets

(56) References Cited

U.S. PATENT DOCUMENTS

| | | | |
|---|---|---|---|
| 5,530,586 A * | 6/1996 | Yasugaki | 359/364 |
| 5,646,597 A * | 7/1997 | Hamburger et al. | 340/627 |
| 5,701,012 A * | 12/1997 | Ho | 250/461.2 |
| 5,808,759 A * | 9/1998 | Okamori et al. | 359/15 |
| 5,808,805 A * | 9/1998 | Takahashi | 359/651 |
| 5,880,891 A * | 3/1999 | Furter | 359/651 |
| 5,895,922 A * | 4/1999 | Ho | 250/492.1 |
| 5,969,622 A * | 10/1999 | Hamburger et al. | 340/627 |
| 5,986,555 A * | 11/1999 | Hamburger et al. | 340/627 |
| 5,999,250 A * | 12/1999 | Hairston et al. | 356/73 |
| 6,008,729 A * | 12/1999 | Hamburger et al. | 340/627 |
| 6,225,046 B1 | 5/2001 | Vesey et al. | 435/5 |
| 6,246,045 B1 | 6/2001 | Morris et al. | 250/216 |
| 6,350,041 B1 * | 2/2002 | Tarsa et al. | 362/231 |
| 6,597,504 B2 * | 7/2003 | Dubin et al. | 359/484.08 |
| 6,876,305 B2 * | 4/2005 | Kadwell et al. | 340/630 |
| 6,999,231 B2 * | 2/2006 | Bryant | 359/359 |
| 7,053,783 B2 * | 5/2006 | Hamburger et al. | 340/630 |
| 7,126,687 B2 * | 10/2006 | Hill et al. | 356/336 |
| 7,136,159 B2 * | 11/2006 | Tsai et al. | 356/237.5 |
| 7,430,046 B2 * | 9/2008 | Jiang et al. | 356/336 |
| 7,554,663 B2 * | 6/2009 | Hairston et al. | 356/417 |
| 7,738,099 B2 * | 6/2010 | Morrell et al. | 356/336 |
| 7,884,998 B2 * | 2/2011 | Armstrong | 359/366 |
| 7,970,028 B2 * | 6/2011 | Kuksenkov et al. | 372/33 |
| 8,338,776 B2 * | 12/2012 | Walt et al. | 250/251 |
| 8,427,641 B2 * | 4/2013 | Babico et al. | 356/336 |
| 8,531,674 B2 * | 9/2013 | Soga et al. | 356/450 |
| 8,628,976 B2 * | 1/2014 | Bolotin et al. | 436/172 |
| 8,647,860 B2 * | 2/2014 | Jiang et al. | 435/288.7 |
| 8,665,536 B2 * | 3/2014 | Armstrong | 359/732 |
| 8,766,191 B2 * | 7/2014 | Xu | 250/339.08 |
| 2002/0118362 A1 * | 8/2002 | Saccomanno | 356/246 |
| 2003/0030783 A1 * | 2/2003 | Roche et al. | 356/39 |
| 2003/0047690 A1 * | 3/2003 | Ishidoya et al. | 250/484.5 |
| 2003/0098422 A1 * | 5/2003 | Silcott et al. | 250/458.1 |
| 2004/0095573 A1 * | 5/2004 | Tsai et al. | 356/237.5 |
| 2004/0159799 A1 * | 8/2004 | Saccomanno | 250/461.1 |
| 2005/0105077 A1 * | 5/2005 | Padmanabhan et al. | 356/39 |
| 2005/0243307 A1 * | 11/2005 | Silcott et al. | 356/73 |
| 2006/0124835 A1 | 6/2006 | Kiyomoto et al. | 250/216 |
| 2006/0158615 A1 | 7/2006 | Williamson | 353/37 |
| 2006/0237665 A1 | 10/2006 | Barney et al. | 250/458.1 |
| 2006/0250606 A1 | 11/2006 | Kaye et al. | 356/73 |
| 2008/0029694 A1 | 2/2008 | Young | 250/239 |
| 2009/0008573 A1 | 1/2009 | Conner | 250/459.1 |
| 2009/0066934 A1 | 3/2009 | Gao et al. | 356/73 |
| 2009/0219530 A1 | 9/2009 | Mitchell et al. | 356/336 |
| 2009/0242799 A1 * | 10/2009 | Bolotin et al. | 250/459.1 |
| 2010/0108910 A1 * | 5/2010 | Morrell et al. | 250/459.1 |
| 2010/0159504 A1 | 6/2010 | Babico et al. | 435/34 |
| 2010/0165341 A1 | 7/2010 | Babico et al. | 356/336 |
| 2010/0200770 A1 | 8/2010 | Brun et al. | 250/492.1 |
| 2010/0227386 A1 * | 9/2010 | Neuzil et al. | 435/288.7 |
| 2011/0036995 A1 * | 2/2011 | Binnie et al. | 250/459.1 |
| 2012/0003627 A1 * | 1/2012 | Scholl et al. | 435/5 |
| 2012/0043476 A1 * | 2/2012 | Salmelainen | 250/458.1 |
| 2012/0120385 A1 * | 5/2012 | Jiang | 356/51 |
| 2012/0161034 A1 * | 6/2012 | Johnson | 250/458.1 |
| 2013/0327929 A1 * | 12/2013 | Ohkubo et al. | 250/228 |

* cited by examiner

CONDENSING-TYPE PORTABLE FLUORESCENCE DETECTION SYSTEM

CROSS-REFERENCES TO RELATED APPLICATION

The present application claims priority under 35 U.S.C. 119(a) to Korean application number 10-2012-0075904, filed on Jul. 12, 2012, in the Korean Intellectual Property Office, which is incorporated by reference in its entirety as if set forth in full.

BACKGROUND OF THE INVENTION

1. Technical Field

The present invention relates to a portable system capable of quickly diagnosing and monitoring pathogenic organs for men and animals on the site, and more particularly, to a condensing-type portable fluorescence detection system capable of detecting antigens using fluorescence at high speed and with high precision. Furthermore, the present invention relates to a condensing-type portable fluorescence detection system which overcomes the limit of a conventional fluorescence detection system having a maximum efficiency of 70% by condensing light directed to the opposite direction of a photodetector using only one dome reflector, and reflects even the fluorescence, which has been discharged from the conventional fluorescence detection system and corresponds to about 30%, using a spherical mirror, thereby theoretically obtaining an efficiency of 100%.

2. Related Art

Conventionally, Greencross MS, Inc. has developed a MITC (Magnetic ImmunoChromatographic Test) system to diagnose cardiovascular disorders from technology transferred from MagnaBioSciences, LLC in US. Furthermore, Boditech Med Inc. and NanoEnTek Inc. have developed a kit to diagnose cardiovascular disorders and the like using a laser bio diagnosis system.

An FICT (Fluorescence ImmunoChromatographic Test) system using laser has been developed by BioSite, Inc. in US and widely released with a product name called Triage. The FICT system having about 4 billion won in sales in Korea is forming a large market. In addition, many companies such as Inverness (US), Roche (Swiss), Abbott (US) are developing a large-scale diagnosis system using fluorescence.

However, in the case of a laser-induced fluorescence detection method which is widely used in the above-described conventional systems, a system for implementing the method has a complex structure. Therefore, the system had difficulties in diagnosing pathogenic organs on the site.

Accordingly, a portable fluorescence detection system to detect antigens at high speed and with high precision has been developed as part of the development for a portable system capable of quickly diagnosing and monitoring pathogenic organs for men and animals on the site.

First, referring to FIGS. 1 to 5, the basic structure and principle of a conventional fluorescence detection system will be described.

As a method of detecting fluorescence on a DNA chip or a protein chip using membrane, the laser-induced fluorescence detection method has been representatively used. The laser-induced fluorescence detection method excites a fluorescent material using laser as an excitation light source having a wavelength at which the fluorescent material is absorbed, measures the intensity of fluorescence emitted while the fluorescent material is moved to a ground state from the excited state, and measures the concentration of the fluorescent material in proportion to the intensity of each fluorescence. In this way, a fluorescent material may be added to a DNA or protein sample to perform quantitative analysis.

FIG. 1 illustrates a confocal laser scanning system 10 which is most frequently used among systems to detect fluorescence using the above-described laser-induced fluorescence detection method.

The confocal laser scanning system 10 receives fluorescence signals emitted from a sample through a photon multiplier tube using laser as a light source, and then converts the received fluorescence signals into a digital image. The confocal laser scanning system 10 excites only light at a wavelength suitable for a fluorescent material on the sample using a laser light source, and induces fluorescence emission. At this time, various types of filters such as a beam splitter may be selected, and a pin hole may be positioned in front of a photodetector so as to receive only a phase of which the focus is adjusted.

FIG. 2 schematically illustrates the entire structure of a conventional laser induced surface fluorescence detection system using an elliptical reflector mirror.

Referring to FIG. 2, the laser induced surface fluorescence detection system 20 generates fluorescence by projecting incident light on a sample arranged at a first focus of an elliptical reflector mirror 23, condenses the fluorescence and scattering light of the incident light on a second focus, and converts the fluorescence into parallel light to detect surface fluorescence. Specifically, light of laser 21 passes through an excitation filer 22, passes through a hole positioned at the middle position of the elliptical reflector mirror 23 disposed between the excitation filter 22 and a sample control unit 24, and is then condensed at a proper size on the surface of the sample fixed to the sample control unit 24.

The condensing point is positioned at the first focus of the elliptical reflector mirror 23. The fluorescence emitted from the first focus and the scattering light of the incident light are reflected by the elliptical reflector mirror 23 and condensed on a pin hole 25 serving as the second focus of the elliptical reflector mirror 23 and removing noise caused by dust or the like on the surface of the sample. Then, the light passing through the pin hole 25 is converted into parallel light by a collimator 26. While the parallel light passes through a fluorescence filter 28, the scattering light is filtered, and only pure fluorescence is incident on a photodetector 27. The fluorescence incident on the photodetector 27 is transmitted as a signal indicating fluorescence intensity to a computer 29 and then analyzed and processed. However, the confocal laser scanning system 10 and the laser-induced detection system 20 have a complex structure including the lens, the beam splitter, the laser and the like, require expensive equipments, and require a long time for detection. Therefore, there is a limitation in using the confocal laser scanning system 10 and the laser induced detection system 20 as an emergency and portable detection kit for various viruses.

As another conventional portable detection system, the present inventors have developed a portable fluorescence detection system as part of the development for a high-speed high-precision multi-antigen diagnosis machine and an early diagnosis system for infectious diseases of men and animals, based on a portable LED light source and a fluorescent substance. The portable fluorescence detection system has been disclosed in Korean Patent Laid-open Publication No. 10-2011-0032688 applied for on Apr. 8, 2011.

FIGS. 3 and 4 schematically illustrate the entire structure of the conventional portable fluorescence detection system proposed by the present inventors.

Referring to FIG. 3, the conventional portable fluorescence detection system 1 conveniently and quickly detects fluorescence of a sample 600 for a DNA chip or protein chip using membrane, and includes a light source 100, a rotating unit 300, a plurality of filter units 200, a curved reflector unit 400, and a photodetector 500.

The light source 100 includes an LED. The LED has a small size, a long lifetime, and various wavelengths, may be purchased at a low price, and has a wide choice of colors from a single color to a white color. Therefore, the LED may be suitably used as the light source of the portable fluorescence detection system 1. In this case, various elements having excellent fluorescence efficiency may be utilized according to LED wavelengths suitable for the respective elements.

Furthermore, a semiconductor laser which is usually used for fluorescence excitation has a limited wavelength range of choice and is very expensive or difficult to supply except for a specific wavelength range, even though it has a much smaller size than an existing gas laser. Therefore, the semiconductor laser is not suitable as the light source of the portable fluorescence detection system 1.

The rotating unit 300 has a plate shape. The filter units 200 are installed on one surface of the rotating unit 300 and selectively filter light emitted from the light source 100. The curved reflector unit 400 includes a mirror which is depressed inward to form a curved surface and installed on the opposite side of the surface of the rotating unit 300, where the filter units 200 are installed. The light source 100 is installed on a predetermined region of the outer surface of the curved surface reflector unit 400.

At this time, the curved reflector unit 400 may include any structures such as hemisphere, semi-ellipse, parabola, and quarter sphere, as long as they have a mirror depressed inward to form a curved surface. The photodetector 500 is installed on the opposite side of the surfaces of the filter units 200 which are contacted with the rotating unit 300, detects an optical signal generated when a fluorescent material of a sample 600 is excited by light generated from the light source 100, and converts the detected optical signal into an electrical signal.

The photodetector 500 may include a diode-type photodetector, a photoconductor-type photodetector, a camera, a CCD sensor, a CMOS sensor or the like, depending on the type of an optical signal to be detected. When a part of the components is removed, colors may be determined through user's naked eyes.

The filter units 200 serve to pass fluorescent light entering the photodetector 500 and block light of the light source 100, and may be installed at a predetermined distance from each other on one surface of the rotating unit 300 so as to transmit different wavelength ranges of fluorescence. At this time, the plurality of filter units 200 may be installed in such a manner that the centers of the filter units 200 are positioned on the same circumference.

Furthermore, the filter units 200 may pass different wavelengths depending on the positions thereof, and may be detachably installed on the rotating unit 300. At this time, the rotating unit 300 may include a rotating shaft 310 installed in the center thereof such that the filter units 200 may be replaced by the rotation of the rotating unit 300. Accordingly, since the filter units 200 can be easily replaced by the rotation of the rotating unit 300, the portable fluorescence detection system 1 may detect a plurality of fluorescences located at various wavelength ranges within a short time, without using a separate spectroscope. Accordingly, diagnosis may be performed quickly.

The curved reflector unit 400 may be installed in the opposite side of the surface of the rotating unit 300 on which the filter units 200 are mounted, such that the center thereof and the center of a filter unit 200 are positioned on the same vertical line. Accordingly, although a filter unit 200 is replaced by the rotation of the rotating unit 300, the center of the curved reflector unit 400 is positioned on the same vertical line as the center of the replaced filter unit 200. Therefore, a process of detecting fluorescence of the sample 600 is performed under the same condition for each of the filter units 200. At this time, the inner surface of the curved reflector unit 400 may be formed of any one of PDMS, epoxy resin, plastic, glass, and metal. When the curved reflector unit 400 is formed of plastic, the unit cost of production may be reduced, and the manufacturing speed may be improved. Accordingly, the reflector units 400 can be mass-produced.

The portable fluorescence detection system 1 may further include a motor installed on the rotating shaft 310 of the rotating unit 300 so as to rotate the rotating unit 300 at a constant speed about the rotating shaft 310.

Hereinafter, the operation of the portable fluorescence detection system 1 will be described as follows. First, fluorescence generated by the light source 100 is reflected by the inner curved surface of the curved reflector unit 400 and propagates toward the photodetector 500 through the filter unit 200. The curved reflecting mirror formed on the inner surface of the curved reflector unit 400 reflects the light of the light source 100 such that the reflected light excites a fluorescent material a plurality of times, thereby increasing the sensitivity of the photodetector 500.

Here, when a spherical mirror is not used as illustrated in FIG. 5A, only a part of light emitted from a fluorescent material is incident on the photodetector. However, when a parabolic mirror is used as illustrated in FIG. 5B, lights directed toward the mirror surface are vertically reflected. Therefore, although the photodetector is positioned at a remote position, at least 50% or more of lights may be detected. Furthermore, when a quarter spherical mirror is used as illustrated in FIG. 5C, lights are not reflected as vertically as the lights are reflected by the elliptical mirror. However, since the lights are relatively vertically reflected, detection efficiency is improved more than when a mirror is not used.

That is, the portable fluorescence detection system disclosed in Korean Patent Laid-open Publication No. 10-2011-0032688 may be conveniently carried because the portable fluorescence detection system does not use a lens and laser so as to be used as a detection kit for various fluorescent materials. Furthermore, since the portable fluorescence detection system may detect a plurality of fluorescences within a short time, diagnosis may be quickly performed. Furthermore, since the portable fluorescence detection system does not use expensive equipments such as lens, laser, and beam splitter, the cost may be reduced.

As described above, the principle that light is condensed by changing the optical path through the spherical or parabolic dome reflector has been proposed. However, the structure of a fluorescence detection system capable of condensing light emitted in every direction from a point light source into one region using spherical mirrors having different shapes and theoretically obtaining an efficiency of 100% and a method for manufacturing the same have never been proposed.

SUMMARY

An embodiment of the present invention is directed to a condensing-type portable fluorescence detection system which overcomes the limit of a conventional fluorescence detection system having a maximum efficiency of 70% by condensing light directed to the opposite direction of a photodetector using only one dome reflector, and condenses light emitted from a point light source in every direction into one region using spherical mirrors having different shapes, thereby theoretically obtaining an efficiency of 100%.

In accordance with an embodiment of the present invention, a condensing-type portable fluorescence detection system which detects antigens using fluorescence includes: a light source generating light to excite a fluorescent substance; a first filter selecting a proper wavelength range from the light generated from the light source; a spherical mirror including two hemispherical mirrors having different curvature radiuses and connected to each other, and condensing the light excited and emitted from the light source; a second filter selecting a proper wavelength range of the light condensed by the spherical mirror; and a photodetector detecting fluorescence from the light condensed by the spherical mirror and passing through the second filter.

In accordance with another embodiment of the present invention, a condensing-type portable fluorescence detection system which detects antigens using fluorescence includes: a spherical mirror condensing light excited and emitted from a fluorescent substrate of a sample; and a photodetector detecting the condensed light, wherein the spherical mirror includes first and second spherical units having different curvature radiuses, and the first and second spherical units are connected to each other such that the focuses thereof coincide with each other.

The spherical mirror may have a connection surface on which the first and second spherical units are connected to each other such that the focuses thereof coincide with each other, and the first and second spherical units may be connected to each other such that the first spherical unit condenses light propagating under the connection surface and the second spherical unit condenses light propagating over the connection surface.

In accordance with the embodiments of the present inventions, as the condensing-type portable fluorescence detection system capable of theoretically obtaining an efficiency of 100% by adding a semispherical mirror to the structure of the conventional fluorescence detection system using only one dome reflector is provided, it is possible to obtain fundamental technology for the bio-diagnosis system including a fluorescent substance for diagnosis and an LED having a wavelength range coinciding with the fluorescent substance.

Furthermore, various advantages of the LED having a variety of wavelengths, a stable optical power, a long lifetime, a small size, a small weight, and a lower price than other light sources may be utilized to significantly reduce the initial purchasing cost and the maintenance cost. Furthermore, it is possible to develop a respiratory infection diagnosis system having high reliability, high precision, and high portability.

BRIEF DESCRIPTION OF THE DRAWINGS

The above and other aspects, features and other advantages of the subject matter of the present disclosure will be more clearly understood from the following detailed description taken in conjunction with the accompanying drawings, in which.

DETAILED DESCRIPTION

Figure 1:
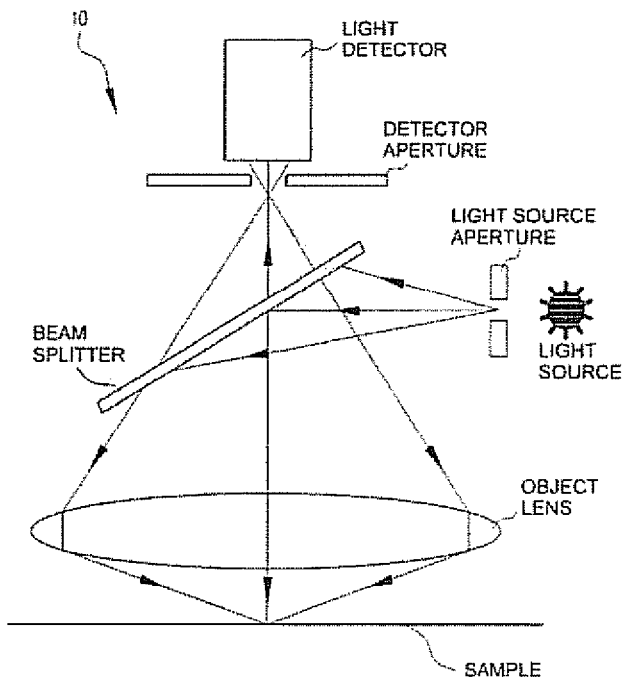
FIG. 1 schematically illustrates the entire structure of a conventional laser-induced fluorescence detection system.
Figure 2:
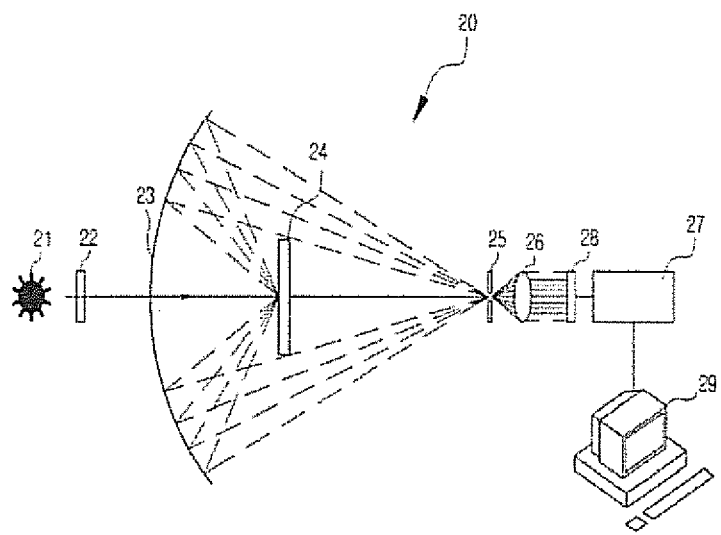
FIG. 2 schematically illustrates the entire structure of a conventional laser-induced surface fluorescence detection system using an elliptical reflector mirror.

Exemplary embodiments of the present invention will be described below in more detail with reference to the accompanying drawings. The present invention may, however, be embodied in different forms and should not be constructed as limited to the embodiments set forth herein. Rather, these embodiments are provided so that this disclosure will be thorough and complete, and will fully convey the scope of the present invention to those skilled in the art. Throughout the disclosure, like reference numerals refer to like parts throughout the various figures and embodiments of the present invention.

The embodiments of the present invention provide a condensing-type portable fluorescence detection system capable of detecting antigens through fluorescence at a high speed and with high precision, in order to develop a portable system capable of quickly diagnosing and monitoring pathogenic organs for men and animals on the site.

Although described below, the condensing-type portable fluorescence detection system in accordance with the embodiment of the present invention includes an excitation light source, an excitation filter, a spherical mirror, an emission filter, and a photodetector. The spherical mirror includes two spherical mirrors which have different curvature radiuses and are connected to each other such that the focuses thereof coincide with each other.

In accordance with the embodiment of the present invention, since the system does not use a lens, the volume of the system may be reduced. Furthermore, since the system condenses light emitted in every direction from a fluorescence source into a specific narrow region through a dome reflector so as to theoretically increase the condensing efficiency of the fluorescence to 100%, the reliability of diagnosis may be increased.

That is, the conventional portable fluorescence detection system condenses light directed toward the opposite direction of the photodetector using one dome reflector, thereby obtaining a maximum efficiency of 70%. In this embodiment of the present invention, however, one semispherical mirror may be additionally used as described below. Therefore, the condensing-type portable fluorescence detection system may reflect even fluorescence which has been discharged by the conventional portable fluorescence detection system and corresponds to about 30% or more of the entire fluorescence, theoretically obtaining an efficiency of 100%.

Referring to the accompanying drawings, the condensing-type portable fluorescence detection system in accordance with the embodiment of the present invention will be described in detail.

The present inventors have suggested a condensing-type portable fluorescence detection system which is capable of theoretically obtaining an efficiency of 100%, as described below.

Figure 3:
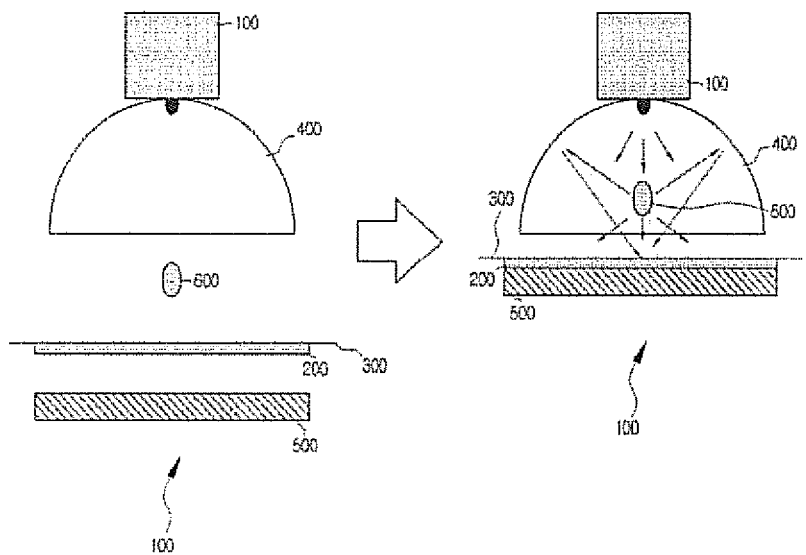
FIG. 3 illustrates the operation principle of a conventional portable fluorescence detection system.
Figure 4:
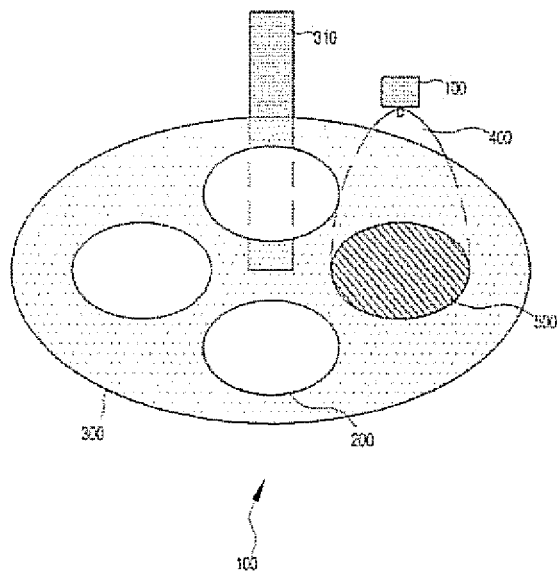
FIG. 4 illustrates the entire structure of the conventional portable fluorescence detection system.
Figure 5A:
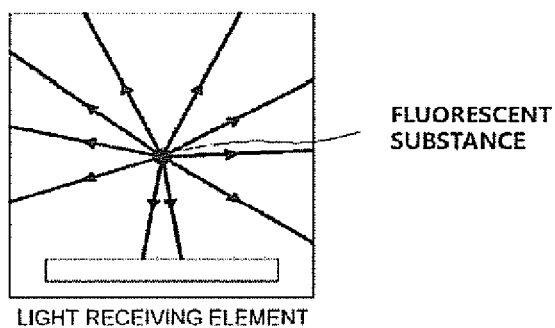
FIG. 5A illustrates propagation of light when the conventional portable fluorescence detection system has no curved reflector mirror.
Figure 5B:
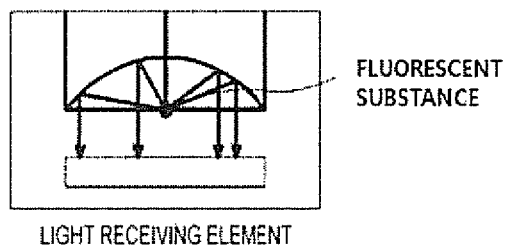
FIG. 5B illustrates propagation of light when a parabolic mirror is used.
Figure 5C:
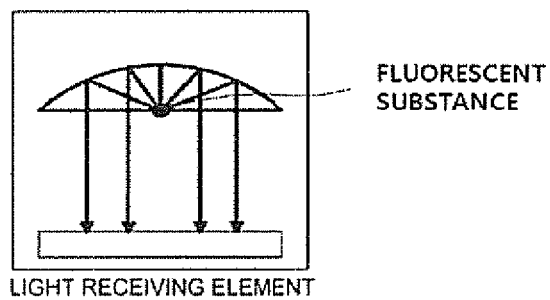
FIG. 5C illustrates propagation of light when a quarter spherical mirror is used.
Figure 6:
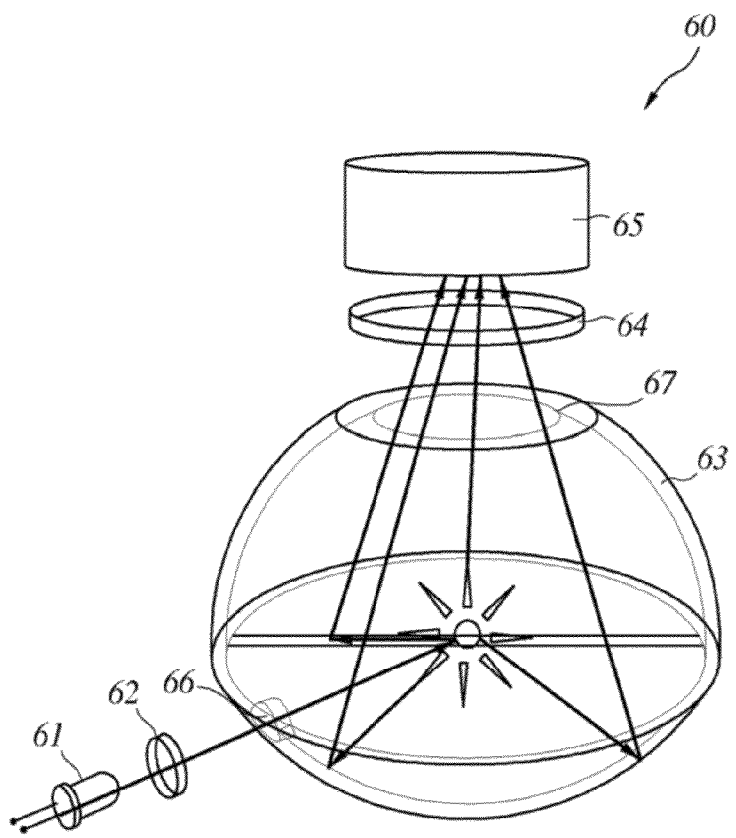
FIG. 6 schematically illustrates the entire structure of a portable fluorescence detection system in accordance with an embodiment of the present invention.

Referring to FIG. 6, the condensing-type portable fluorescence detection system 60 in accordance with the embodiment of the present invention will be described in detail. Here, the detailed descriptions of the same components as those of the conventional portable fluorescence detection system 1 described with reference to FIGS. 3 to 5 are omitted, and the following descriptions will be focused on different components.

The condensing-type portable fluorescence detection system 60 in accordance with the embodiment of the present invention may include a non-imaging system using an integrating sphere having two spherical mirrors bonded thereto.

In the case of a virus which has been completely analyzed in a laboratory, a complex image does not need to be obtained, but only infection may be examined in the farming and fishing villages where a virus or infectious disease must be detected. Therefore, a lens for imaging is not necessary in detection fields where imaging is not necessarily required. Furthermore, when a spherical mirror structure to condense light emitted in every direction into one point is used to condense fluorescence, detection efficiency may be improved as much.

Referring to FIG. 6, the condensing-type portable fluorescence detection system 60 in accordance with the embodiment of the present invention includes a fluorescence excitation source 61, an excitation filter 62, a spherical mirror 63, an emission filter 64, and a photodetector 65. The fluorescence excitation source 61 generates excitation light to excite a fluorescent substance. The excitation filter 62 selectively filters the light generated from the fluorescence excitation source 61. The spherical mirror 63 condenses light emitted from a sample by the light transferred from the fluorescent excitation source 61. The emission filter 64 filters the light condensed by the spherical mirror 63. The photodetector 65 detects fluorescence through the condensed light.

Referring to FIG. 6, the spherical mirror 63 includes a light entrance 66 on which light generated from the excitation source 61 is incident and a light exit 67 from which light condensed inside the spherical mirror 63 is discharged.

The fluorescence excitation source 61 may include an LED instead of a laser which is generally used. The LED has a small size and a long lifetime, and may be easily purchased at a low price. Therefore, the fluorescence excitation source 61 including an LED may be favorably applied to the portable detection system for detecting pathogenic organs on the site. Accordingly, the portable detection system may have more excellent portability and more competitive price than the conventional portable detection system. Furthermore, the excitation filter 62 and the emission filter 64 may be selectively installed depending on the fluorescent characteristic of each sample. Therefore, crosstalk may be minimized, and light having a wavelength suitable for the fluorescent characteristic of the corresponding sample may be supplied to the sample and reach the photodetector 65.

Here, when a sample is changed, that is, when a fluorescent substance is changed, the condensing-type portable fluorescence detection system 60 requires a filter suitable for the emission wavelength of the corresponding fluorescent substance. Therefore, the condensing-type portable fluorescence detection system 60 may further include a filter rotating unit to rotate a filter. Therefore, a proper filter may be selected from a plurality of filters installed in the condensing-type portable fluorescence detection system 60.

Since the filter rotating unit has the same structure as the rotating unit of the conventional portable fluorescence detection system illustrated in FIG. 4, the detailed descriptions thereof are omitted herein.

The spherical mirror 63 serves to condense light emitted from a sample, that is, a fluorescent substance. As described above, the fluorescent substance emits light in every direction. Therefore, when a general method is used, only a part of the emitted light reaches the photodetector. However, since the spherical mirror 63 in accordance with the embodiment of the present invention has a structure in which two spherical mirrors having different curvature radiuses are connected to each other such that the focuses thereof coincide with each other as illustrated in FIG. 6, the spherical mirror 63 may theoretically condense 100% of the emitted light such that the condensed light propagates toward the photodetector. In this respect, the condensing-type portable fluorescence detection system 60 is different from the conventional portable fluorescence detection system.

Figure 7:
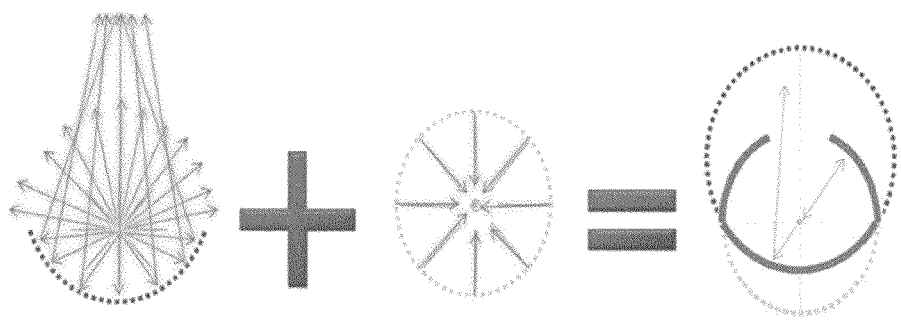
FIG. 7 schematically illustrates a spherical mirror of the portable fluorescence detection system in accordance with the embodiment of the present invention.

More specifically, referring to FIG. 7, the spherical mirror 63 includes a dome reflector and a hemisphere reflector. When the dome reflector is used, all of light directed downward is redirected upward, but light directed upward spreads in every direction. When the hemisphere reflector is used, light starting from the center is reflected by the dome reflector and returns to the center. When parts of the two spherical mirrors are properly combined, fluorescence starting from the center may be directed toward the light entrance 67. As a result, both of excitation light reflected by the reflector dome and excitation light reflected by the hemisphere reflector are directed toward the light exit 67 at the top of the dome reflector and then condensed. The dome reflector condenses light propagating under the sample toward the light exit 67, and the spherical reflector condenses light propagating over the sample toward the light exit 67. Therefore, the sample may be positioned on a virtual connection surface formed between the dome reflector and the spherical reflector.

Based on the above-described principle, a dome reflector and a semispherical mirror having different curvature radiuses were connected to each other to construct the spherical mirror, and light tools were used to perform a simulation.

Hereinafter, referring to FIGS. 8A to 8D, the simulation for implementing the spherical mirror formed by connecting the dome reflector and the semispherical reflector having different curvature radiuses will be described in detail.

Figure 8A:
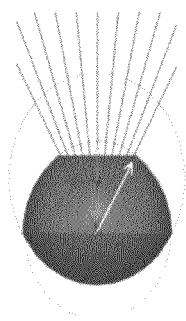
FIGS. 8A to 8D are diagrams for explaining the spherical mirror of the portable fluorescence detection system in accordance with the embodiment of the present invention.
Figure 8B:
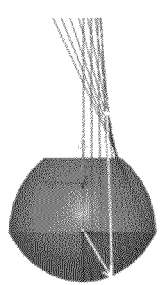
Figure 8C:
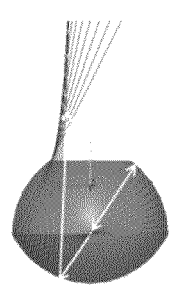

Referring to FIG. 8A, all of fluorescence which is not reflected by the spherical mirror but directed to an upper opening from the center of the spherical mirror escapes through the upper opening. Furthermore, referring to FIG. 8B, all of fluorescent directed to the bottom of the sample from the center of the spherical mirror is reflected by the dome reflector and then directed upward. Furthermore, referring to FIG. 8C, all of fluorescence directed to the semispherical reflector from the center of the spherical mirror is reflected by the semispherical mirror, and then directed upward through the path illustrated in FIG. 8B via the center.

Figure 8D:
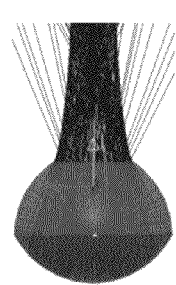

Therefore, when the above-described three cases are combined, light starting in every direction from the center of the spherical mirror may be condensed upward as illustrated in FIG. 8D. That is, since light incident in parallel to the connection surface from the light source is trapped in the structure, light escaping to the outside is minimized. This may work favorably when excitation light starting from the light source and emission light coming from fluorescence are distinguished, that is, filtering is performed. Furthermore, when light coming from the light source is trapped in the spherical mirror structure as described above, the probability that the light will meet the center, that is, the sample again increases as much.

Figure 9A:
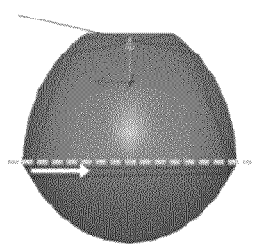
FIGS. 9A to 9C are diagrams illustrating how light coming from a light source propagates inside the spherical mirror.
Figure 9B:
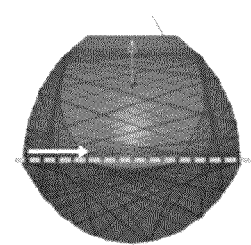
Figure 9C:
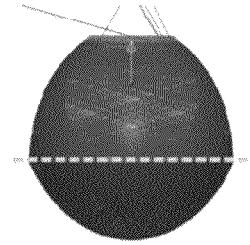

FIGS. 9A to 9C are diagrams illustrating how light coming from the light source propagates inside the spherical mirror. In the spherical mirror in accordance with the embodiment of the present invention, the dome reflector and the hemispherical reflector have different curvature radiuses based on the connection surface. Therefore, when light is incident from a side of the spherical mirror, the light is trapped inside the spherical mirror structure for a quite long time while propagating along a trapezoid optical path as illustrated in FIGS. 9A to 9C.

FIG. 9A illustrates that light propagating in parallel to the connection surface under the connection surface forms a trapezoid optical path. FIG. 9B illustrates that light propagating in parallel to the connection surface over the connection surface reciprocates a plurality of times inside the spherical mirror before the light escapes from the spherical mirror. FIG. 9C illustrates how light incident along the connection surface propagates.

As described above, two semispherical mirrors having different curvature radiuses are connected in such a manner that the focuses thereof coincide with each other, thereby implementing the spherical mirror 63 in accordance with the embodiment of the present invention. The spherical mirror may be formed of various materials such as plastic, metal, glass, and polymer. Desirably, when the spherical mirror 63 is formed of plastic, the spherical mirror 63 may have relatively excellent surface roughness. Furthermore, since the spherical mirror 63 can be easily manufactured at a low cost, the spherical mirror 63 may be mass-produced. Furthermore, the inner surface of the spherical mirror 63 may be coated with aluminum (Al), gold (Au), silver (Ag) or the like, in order to increase the reflectance of the spherical mirror 63.

Figure 10:
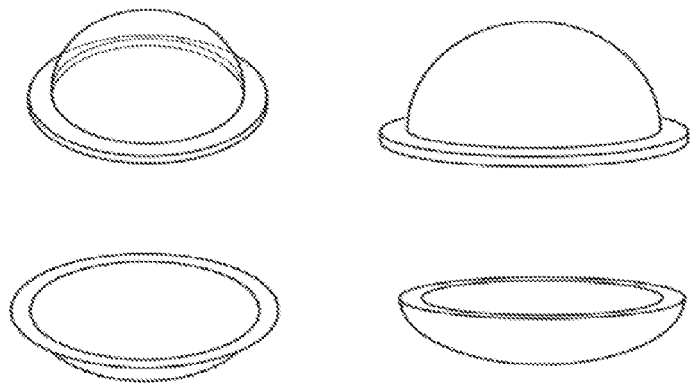
FIG. 10 is a diagram illustrating a method for manufacturing the spherical mirror of the portable fluorescence detection system in accordance with the embodiment of the present invention.
Figure 10:
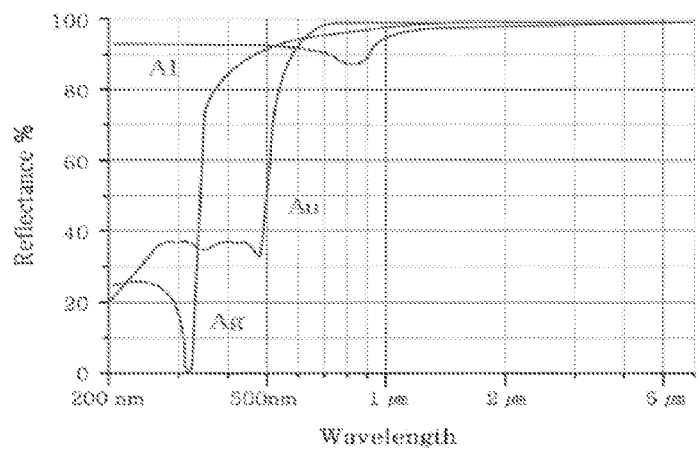

FIG. 10 is a diagram illustrating a method for manufacturing the spherical mirror of the portable fluorescence detection system in accordance with the embodiment of the present invention. Referring to FIG. 10, when the surface of the spherical mirror formed of plastic is coated with Ag, the reflectance may be increased up to 90% with respect to a specific wavelength.

Figure 11:
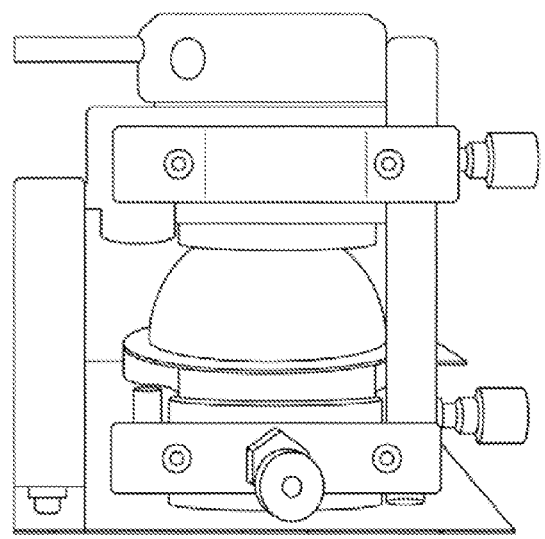
FIG. 11 is a diagram illustrating a measuring device for testing performance of the portable fluorescence detection system in accordance with the embodiment of the present invention.

In order to test the performance of the condensing-type portable fluorescence detection system in accordance with the embodiment of the present invention, an actual fluorescence detection system was implemented as illustrated in FIG. 11, and the performance of the fluorescence detection system was tested through measurement.

Referring to FIGS. 11 to 14, test results obtained by testing the performance of the condensing-type portable fluorescence detection system in accordance with the embodiment of the present invention will be described.

FIG. 11 is a diagram illustrating a measuring device for testing performance of the portable fluorescence detection system in accordance with the embodiment of the present invention.

Referring to FIG. 11, a light source, a filter, a spherical mirror, and a photodetector are disposed to implement a fluorescence detection system for measuring photocurrent, based on the descriptions for the embodiment of the present invention.

In this experimental example, a hemisphere was manufactured to have a diameter of about 2 cm, in order to manufacture the fluorescence detection system based on existing optical parts. However, when the parts are optimized through integration as described below, the hemisphere may be manufactured to have a smaller diameter.

Figure 12:
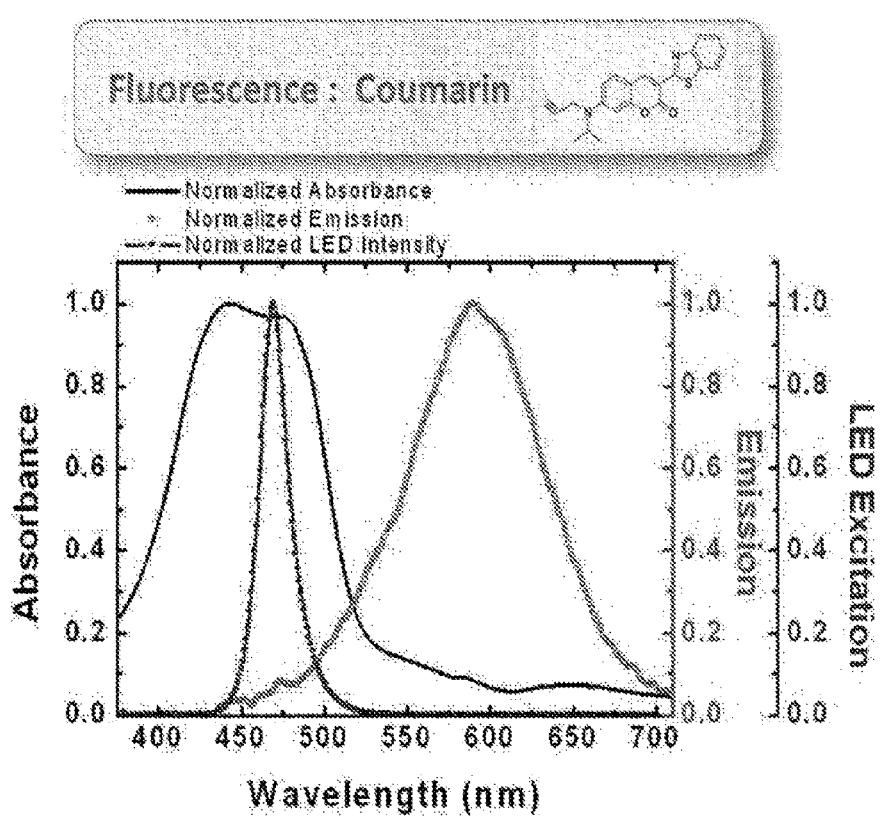
FIG. 12 is a graph illustrating an absorbance wavelength and emission wavelength of fluorescence and an excitation wavelength of an LED when the measuring device illustrated in FIGS. 11 and 12 is used to measure the fluorescence.
Figure 13:
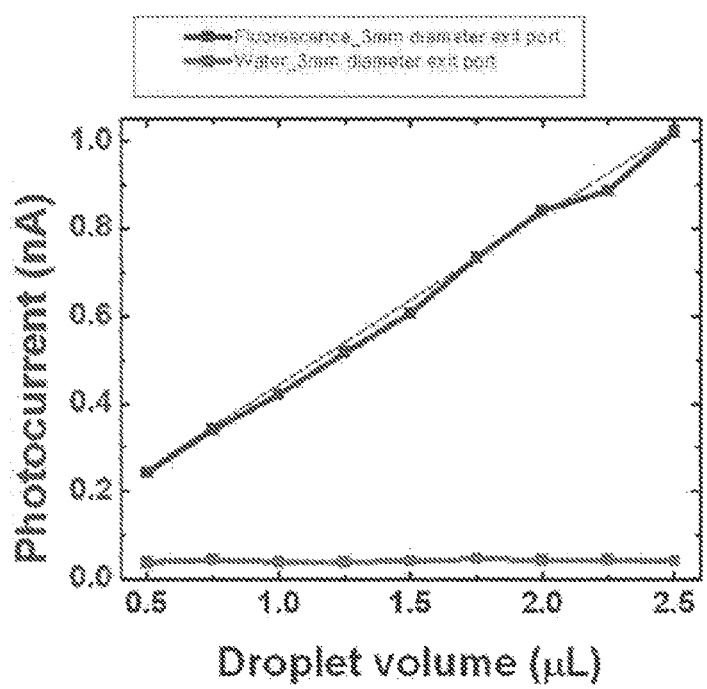
FIG. 13 is a graph illustrating a result obtained by measuring photocurrent while a droplet size is changed in a state where the mole concentration of fluorescence is constantly set.

FIGS. 12 and 13 illustrate results obtained by measuring fluorescence using the measuring device illustrated in FIG. 11.

FIG. 12 is a graph illustrating an absorbance wavelength and emission wavelength of fluorescence and an excitation wavelength of an LED when the measuring device illustrated in FIG. 11 is used to measure the fluorescence. FIG. 13 is a graph illustrating a result obtained by measuring photocurrent while the droplet size is changed in a state where the mole concentration of the fluorescence is constantly set.

In FIG. 12, a coumarin-derivative was used as the fluorescence, and an excitation filter and an emission filter were used to minimize crosstalk with respect to the absorbance wavelength and emission wavelength of the fluorescence and the excitation wavelength of the LED.

In FIG. 13, the mole concentration of the fluorescence was constantly set to $40 \times 10^{-6}$M [40 µM], and the photocurrent was measured while the droplet size is changed. As a comparison group, a test in which only a water drop was applied was performed together.

Therefore, as the condensing-type portable fluorescence detection system using the spherical mirror is manufactured by applying the dome reflector instead of a lens, the amount of fluorescence to be received becomes larger than when a lens is used to obtain an image. Therefore, the condensing efficiency of the detection system may be increased.

Furthermore, since the condensing-type portable fluorescence detection system has a small size and may be conveniently carried, the condensing-type portable fluorescence detection system is suitable for onsite diagnoses for infectious viruses which must be suppressed at the initial stage. Furthermore, since the spherical mirror is formed of plastic and an LED is used as the light source, the condensing-type portable fluorescence detection system has more excellent performance for money than a lens-based detection system requiring a minute hole.

Therefore, when the condensing-type portable fluorescence detection system in accordance with the embodiment of the present invention is implemented as described above, the condensing-type portable fluorescence detection system may reflect even the fluorescence which has been discharged in the conventional portable fluorescence detection system and corresponds to about 30% or more of the entire fluorescence, thereby theoretically obtaining an efficiency of 100%.

So far, the condensing-type portable fluorescence detection system in accordance with the embodiment of the present invention has been described in detail, but the present invention is not limited to the above-described embodiment.

The condensing-type portable fluorescence detection system in accordance with the embodiment of the present invention may be implemented to have a simpler structure through integration of a light source and a detecting unit.

Figure 14A:
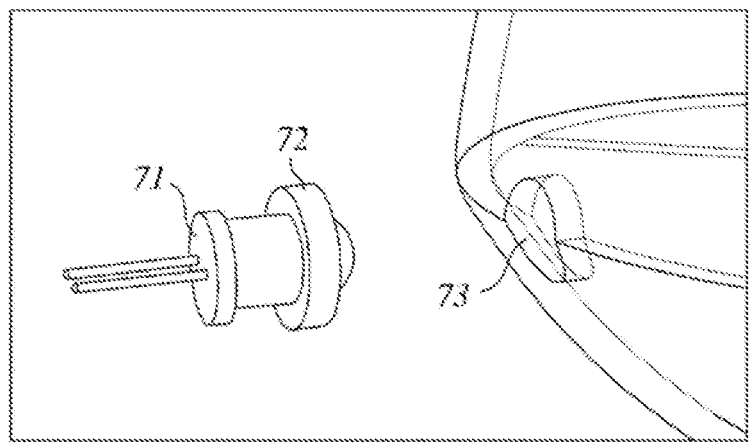
FIGS. 14A and 14B illustrate a condensing-type portable fluorescence detection system in accordance with another embodiment of the present invention.
Figure 14B:
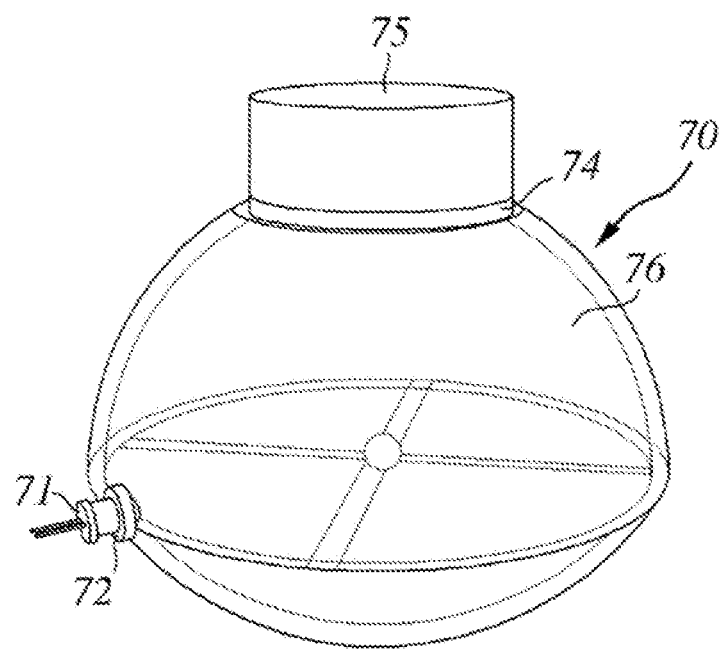

FIGS. 14A and 14B illustrate a condensing-type portable fluorescence detection system in accordance with another embodiment of the present invention. The condensing-type portable fluorescence detection system in accordance with the embodiment of the present invention includes a light source and a photodetector which are integrated with a spherical mirror.

Referring to FIG. 14A, an LED 71 and an excitation filter 72 are integrated and installed at a light entrance 73. Referring to FIG. 14B, an emission filter 74 and a photodetector are installed at a light exit so as to be integrated with the spherical mirror 76. Therefore, unnecessary portions may be removed to implement the condensing-type portable fluorescence detection system 70 having a simpler structure.

While the present invention has been described with respect to the specific embodiments, it will be apparent to those skilled in the art that various changes and modifications may be made without departing from the spirit and scope of the invention as defined in the following claims.

What is claimed is:

1. A condensing-type portable fluorescence detection system which detects antigens using fluorescence, comprising:
   a light source to emit a light;
   a first filter to receive the light and selectively pass a first wavelength range of light, wherein the first wavelength range of light is to cause a fluorescent substance to emit a fluorescent light;
   a spherical mirror to contain the fluorescent substance on a plane passing through the spherical mirror, the spherical mirror comprising:
      a dome reflector having a first radius of curvature, and
      a hemispherical reflector having a second radius of curvature different from the first radius of curvature,
   wherein the dome reflector and the hemispherical reflector connected to each other in the plane, and
   wherein the radius of curvature of the dome reflector and the radius of curvature of the hemispherical reflector are configured to cause a path of the fluorescent light to travel a plurality of generally trapezoidal-shaped optical paths to condense the fluorescent light toward a light exit of the spherical mirror;
   a second filter, located proximate the light exit of the spherical mirror, to receive the fluorescent light and selectively pass a second wavelength range of light; and
   a photodetector, located proximate to the second filter, to detect the second wavelength range of light to identify the fluorescent substance,
   wherein the spherical mirror comprises a light entrance to admit the first wavelength range of light into the spherical mirror, and
   wherein the light exit is formed in the dome reflector.

2. The fluorescence detection system of claim 1, wherein the light source comprises an LED.

3. The fluorescence detection system of claim 1, wherein the first filter and the second filter each comprises:
   a plurality of different selectable filter elements, wherein a selectable filter element is selected to match a characteristic of the fluorescent substance.

4. The fluorescence detection system of claim 1, wherein the first filter and the second filter each comprises:
   a filter rotating unit containing selectable filter elements, wherein a selectable filter element is selected by rotating the filter rotating unit.

5. The condensing-type portable fluorescence detection system of claim 1, wherein the hemispherical reflector condenses a portion of the fluorescent light that is reflected below the plane toward the light exit and the dome reflector reflects fluorescent light toward the hemispherical reflector.

6. The fluorescence detection system of claim 5, wherein the spherical mirror is formed of at least one of plastic, metal, glass, or polymer.

7. The fluorescence detection system of claim 6, wherein the spherical mirror has an inner surface coated with at least one of aluminum (Al), gold (Au), or silver (Ag) to increase reflectance.

8. The fluorescence detection system of claim 5, wherein the spherical mirror is formed of plastic and has an inner surface coated with silver (Ag).

9. The fluorescence detection system of claim 1, wherein the light source and the first filter are integrated and installed at a light entrance of the spherical mirror, and
   the second filter and the photodetector are integrated and installed at the light exit of the spherical minor.

10. The condensing-type portable fluorescence detection system of claim 5, wherein the reflector is a parabolic reflector.

* * * * *